United States Patent [19]
Ray et al.

[11] Patent Number: 5,562,736
[45] Date of Patent: Oct. 8, 1996

[54] METHOD FOR SURGICAL IMPLANTATION OF A PROSTHETIC SPINAL DISC NUCLEUS

[75] Inventors: Charles D. Ray, Golden Valley; Eugene A. Dickhudt, New Brighton, both of Minn.

[73] Assignee: RayMedica, Inc., St. Anthony, Minn.

[21] Appl. No.: 324,138

[22] Filed: Oct. 17, 1994

[51] Int. Cl.⁶ ........................................ A61F 2/44
[52] U.S. Cl. ............................ 623/17; 606/61; 606/99; 606/184
[58] Field of Search ................. 623/17; 606/1, 606/61, 79, 99, 184, 185

[56] References Cited

U.S. PATENT DOCUMENTS

| | | | |
|---|---|---|---|
| 4,545,374 | 10/1985 | Jacobson | 606/61 |
| 4,573,448 | 3/1986 | Kambin | 606/79 |
| 4,772,287 | 9/1988 | Ray et al. | 623/17 |
| 4,904,260 | 2/1990 | Ray et al. | 623/17 |
| 5,019,081 | 5/1991 | Watanabe | 606/79 |
| 5,192,326 | 3/1993 | Bao et al. | 623/17 |
| 5,242,443 | 9/1993 | Kambin | 606/60 |
| 5,306,309 | 4/1994 | Wagner et al. | 623/17 |
| 5,314,477 | 5/1994 | Marnay | 623/17 |
| 5,395,317 | 3/1995 | Kambin | 604/51 |

FOREIGN PATENT DOCUMENTS

| | | | |
|---|---|---|---|
| 92010982 | 7/1992 | WIPO | 623/17 |

OTHER PUBLICATIONS

*Clinical Efficacy and Outcome in the Diagnosis and Treatment of Low Back Pain*, specifically Chapter 21, Charles Dean Ray, *The Artificial Disc, Introduction, History and Socioeconomics*, 1992, pp. 205–225.

*Primary Examiner*—Michael J. Milano
*Attorney, Agent, or Firm*—Kinney & Lange

[57] ABSTRACT

A method for surgically implanting a prosthetic spinal disc nucleus body into a human spinal disc space is disclosed. The spinal disc space contains adjacent vertebrae and an anulus having a posterior side. The method includes cutting a flap through the anulus in the disc space to create an opening. The vertebrae adjacent to the disc space are slightly separated and a prosthetic spinal disc nucleus body is inserted through the opening into the disc space.

17 Claims, 10 Drawing Sheets

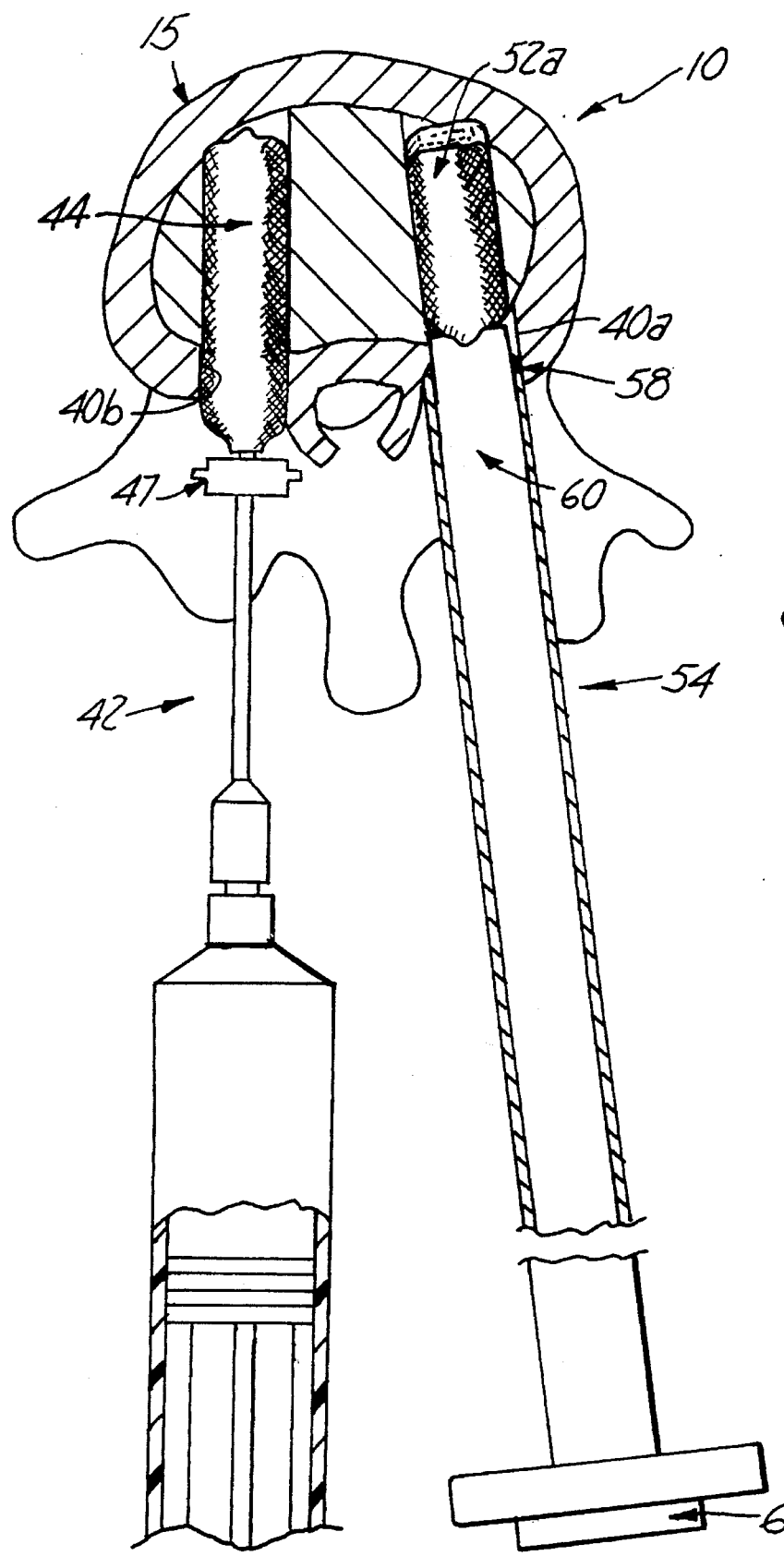

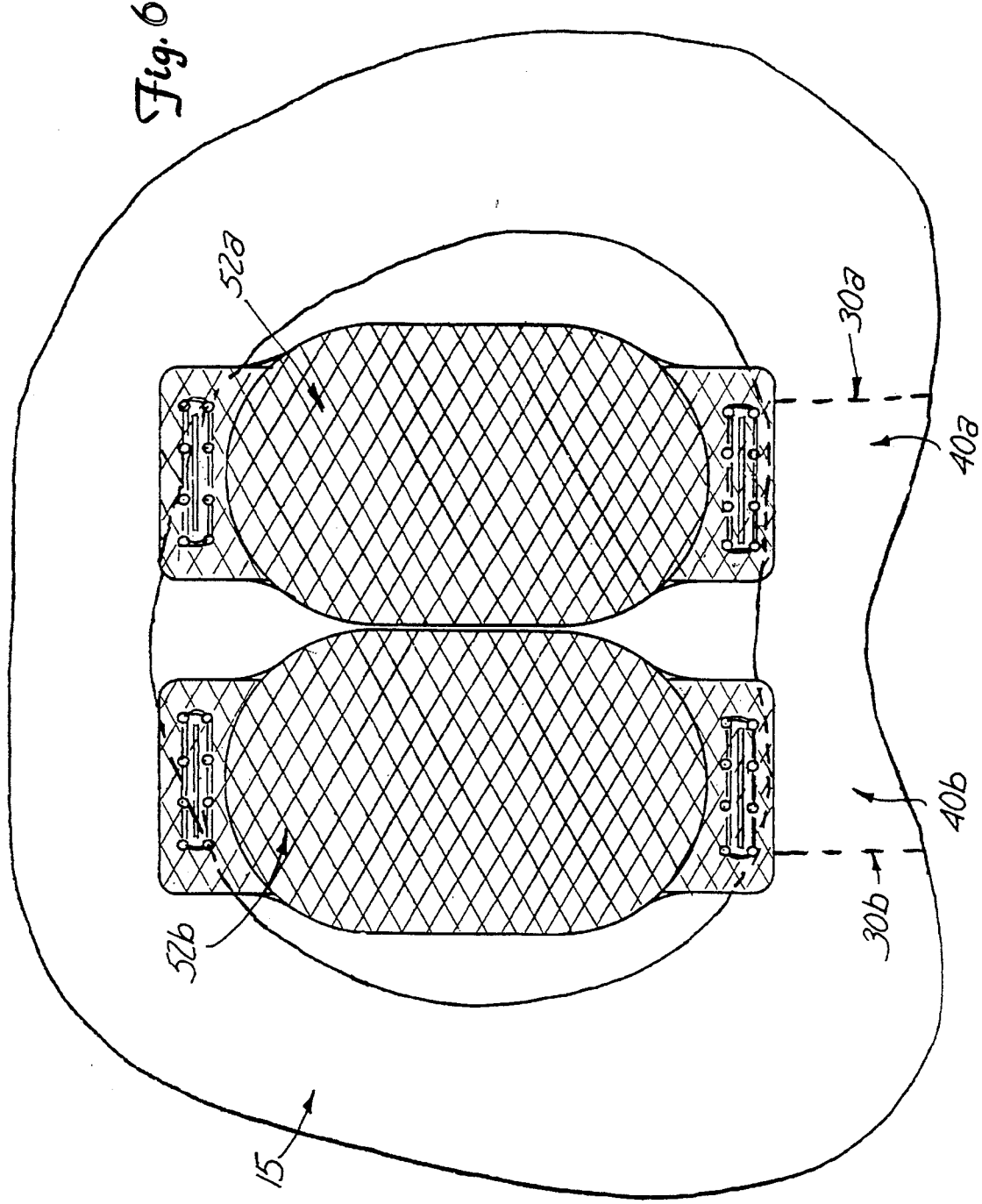

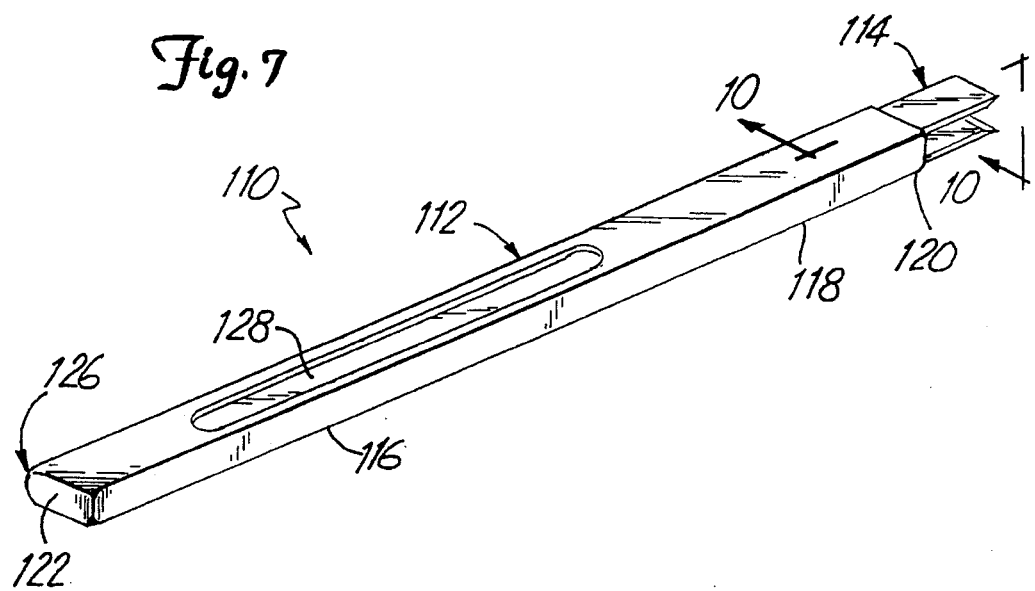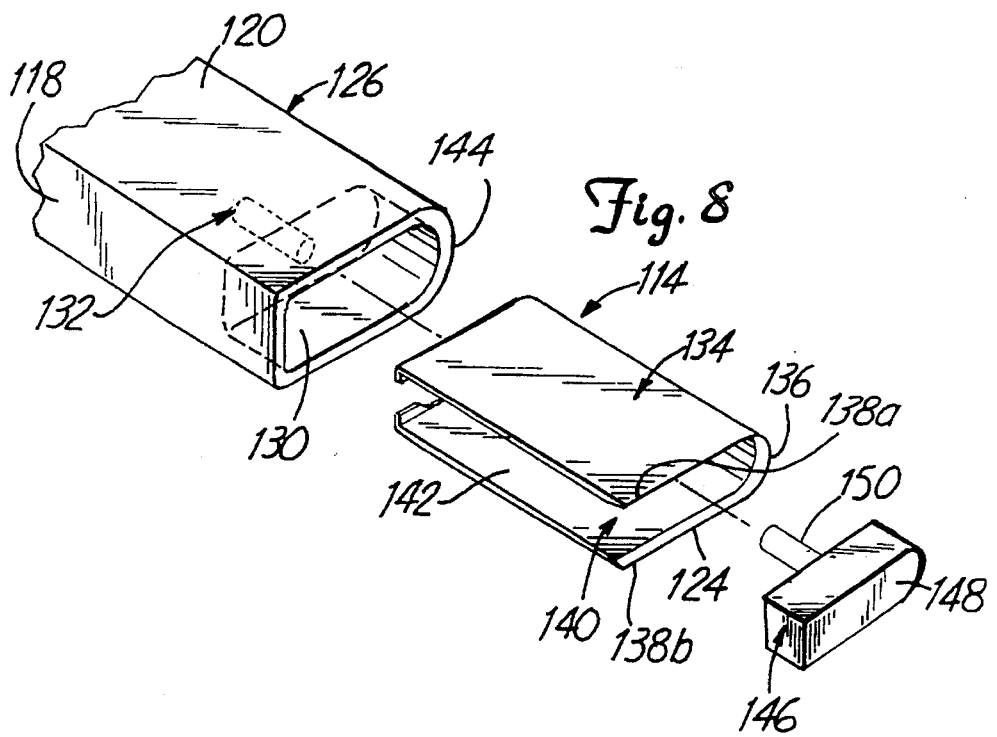

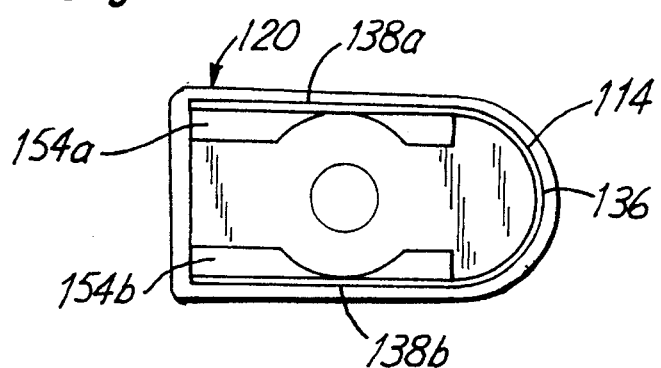
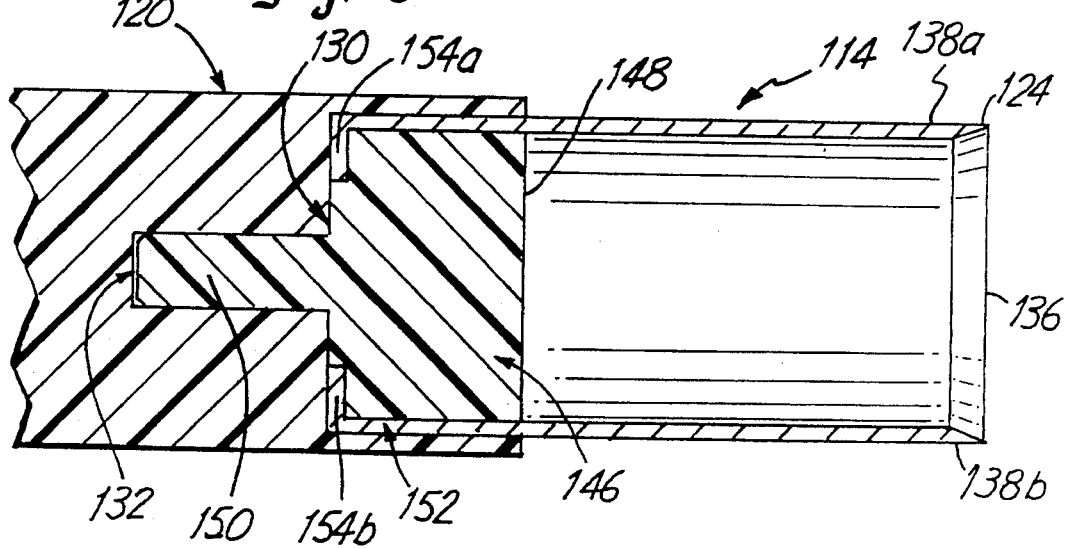

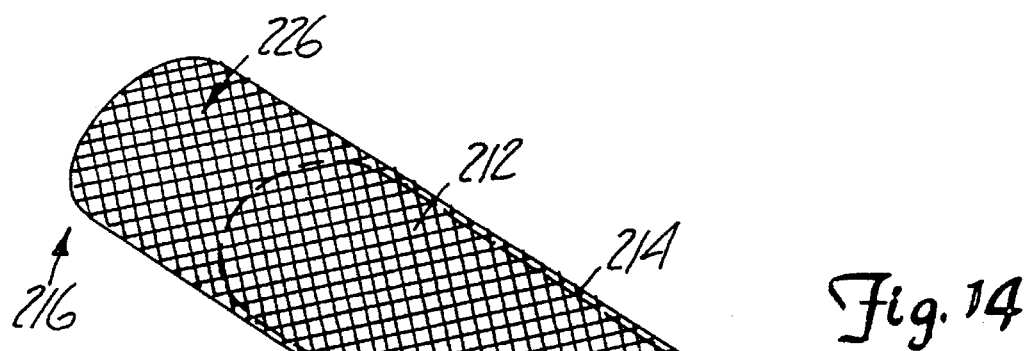
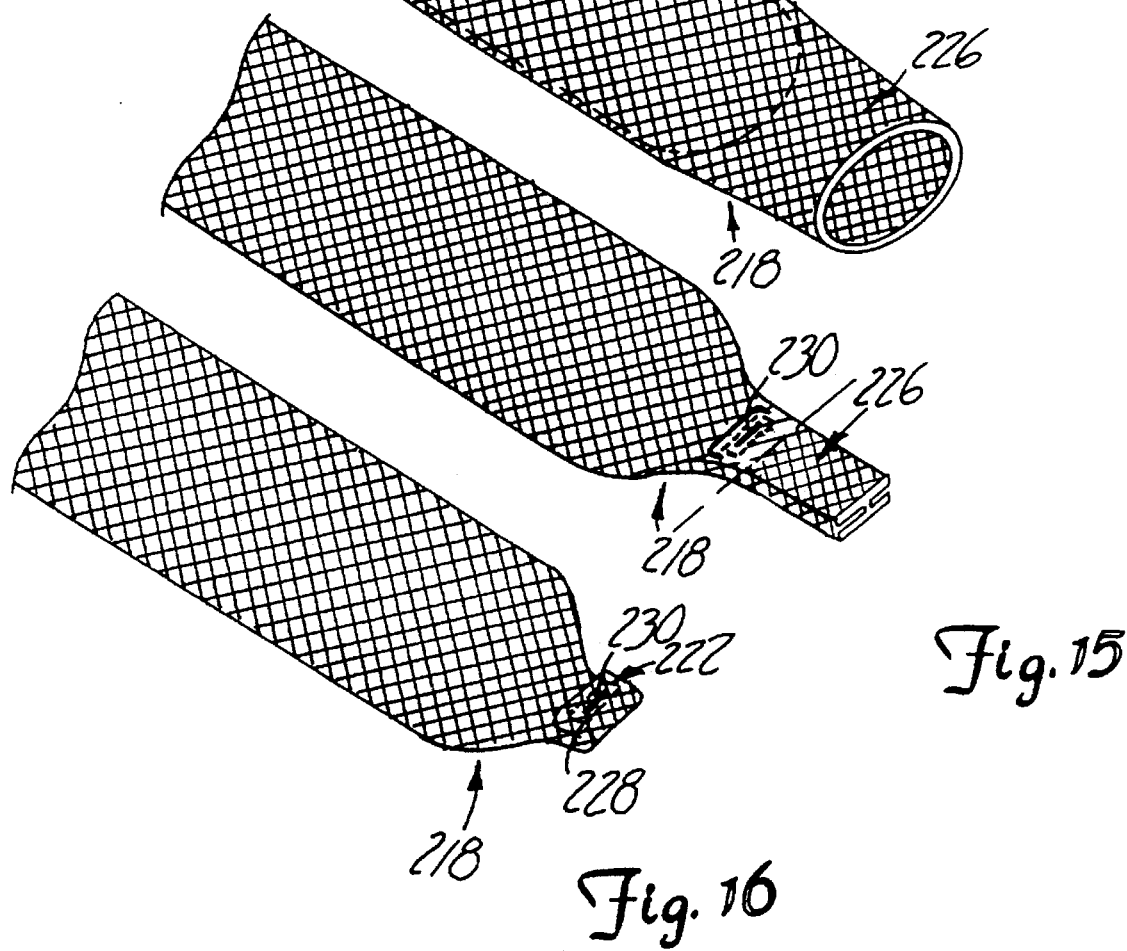

METHOD FOR SURGICAL IMPLANTATION OF A PROSTHETIC SPINAL DISC NUCLEUS

BACKGROUND OF THE INVENTION

Co-pending patent applications entitled "Prosthetic Spinal Disc Nucleus" and "Spinal Anulus Cutter" were filed on the same day as the present application and are assigned to the same assignee.

The present invention concerns a surgical method for implanting a prosthetic spinal disc nucleus into a human spinal disc space. More particularly, it relates to the implantation of pillow shaped prosthetic spinal disc nucleus bodies into a degenerated intervertebral disc space.

The vertebrate spine is the axis of the skeleton on which all of the body parts "hang". In humans, the normal spine has seven cervical, twelve thoracic and five lumbar segments. The lumbar spine sits upon the sacrum, which then attaches to the pelvis, in turn is supported by the hip and leg bones. The bony vertebral bodies of the spine are separated by intervertebral discs, which act as joints but allow known degrees of flexion, extension, lateral bending, and axial rotation.

The typical vertebra has a thick anterior bone mass called the vertebral body, with a neural (vertebral) arch that arises from the posterior surface of the vertebral body. The centra of adjacent vertebrae are supported by intervertebral discs. Each neural arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch which extends posteriorly and acts to protect the spinal cord's posterior side is known as the lamina. Projecting from the posterior region of the neural arch is the spinous process.

The intervertebral disc primarily serves as a mechanical cushion permitting controlled motion between vertebral segments of the axial skeleton. The normal disc is a unique, mixed structure, comprised of three component tissues: the nucleus pulpous ("nucleus"), the anulus fibrosus ("anulus") and two vertebral end plates. The two vertebral end plates are composed of thin cartilage overlying a thin layer of hard, cortical bone which attaches to the spongy, richly vascular, cancellous bone of the vertebral body. The end plates thus acts to attach adjacent vertebrae to the disc. In other words, a transitional zone is created by the end plates between the malleable disc and the bony vertebrae.

The anulus of the disc is a tough, outer fibrous ring which binds together adjacent vertebrae. The fibrous portion, which is much like a laminated automobile tire, measures about 10 to 15 millimeters in height and about 15 to 20 millimeters in thickness. The fibers of the anulus consist of fifteen to twenty overlapping multiple plies, and are inserted into the superior and inferior vertebral bodies at roughly a 40 degree angle in both directions. This configuration particularly resists torsion, as about half of the angulated fibers will tighten when the vertebrae rotates in either direction, relative to each other. The laminated plies are less firmly attached to each other.

Immersed within the anulus, positioned much like the liquid core of a golf ball, is the nucleus. The healthy nucleus is largely a gel-like substance having a high water content, and like air in a tire, serves to keep the anulus tight yet flexible. The nucleus-gel moves slightly within the anulus when force is exerted on the adjacent vertebrae while bending, lifting, etc.

The spinal disc may be displaced or damaged due to trauma or a disease process. A disc herniation occurs when the anulus fibers are weakened or torn and the inner tissue of the nucleus becomes permanently bulged, distended, or extruded out of its normal, internal anulus confines. The mass of a herniated or "slipped" nucleus tissue can compress a spinal nerve, resulting in leg pain, loss of muscle control, or even paralysis. Alternatively, with discal degeneration, the nucleus loses its water binding ability and deflates, as though the air had been let out of a tire. Subsequently, the height of the nucleus decreases causing the anulus to buckle in areas where the laminated plies are loosely bonded. As these overlapping laminated plies of the anulus begin to buckle and separate, either circumferential or radial anular tears may occur, which may contribute to persistent and disabling back pain. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate back pain from degenerated or herniated discs, the nucleus is removed and the two adjacent vertebrae are surgically fused together. While this treatment alleviates the pain, all discal motion is lost in the fused segment. Ultimately this procedure places a greater stress on the discs adjacent to the fused segment as they compensate for lack of motion, perhaps leading to premature degeneration of those adjacent discs.

As an alternative to vertebral fusion, various prosthetic discs have been developed. The first prosthetics embody a wide variety of ideas, such as ball bearings, springs, metal spikes and other perceived aids. These prosthetics are all made to replace the entire intervertebral disc space and are large and rigid. Beyond the questionable applicability of the devices is the inherent difficulties encountered during implantation. Due to their size and inflexibility, these devices require an anterior implantation approach as the barriers presented by the lamina and, more importantly, the spinal cord and nerve rootlets during posterior implantation cannot be avoided.

Anterior implantation, however, is highly suspect and introduces numerous risks. Various organs present physical obstacles as the surgeon attempts to access the damaged disc area. After an incision into the patient's abdomen, the surgeon is forced to engage the interfering organs and carefully move them aside. Ultimately the patient faces the brunt of the anterior approach risk should any organ be damaged.

An additional surgical concern, not previously addressed, is the potential damage imparted upon the anulus during implantation surgery. The normal anular plies act to keep the anulus tight about the nucleus. During surgery, a surgical knife or tool is used to completely sever some portion of the anulus and/or remove an entire section or a "plug" of the anulus tissue. When an entire section of the anulus is cut or removed to insert the prosthetic device, the layers making up the anulus "flay" and/or "pull back" and the constraining or tightening ability of that portion of the anulus is lost. Further, the chances of the anulus healing with restoration of full strength are greatly diminished, while the likelihood of nucleus reherniation is increased. An even greater concern arises where a significant portion of the anulus is removed entirely. A more desirable solution is to leave the anulus at least partially intact during and after implantation.

Recently, smaller and more flexible prosthetic nucleus bodies have been developed. With the reduction in prosthetic size, the ability to work around the spinal cord and nerve rootlets during posterior implantation has become possible.

While the posterior approach to intervertebral disc implantation does have potential difficulties, it is far more desirable than the anterior approach. Additionally, preserving the integrity of the anulus during implant enhances physical healing in the disc area. Therefore, a substantial need exists for a method of surgically implanting a prosthetic spinal disc nucleus body into the intervertebral disc space through a preferably posterior approach, with minimal damage to the anulus.

SUMMARY OF THE INVENTION

The invention provides a method of implanting a prosthetic spinal disc nucleus body into a degenerated intervertebral disc space. The surgical method involves cutting a flap through a portion of the anulus. The flap is peeled back or opened to create an opening through the anulus.

A prosthetic spinal disc nucleus body is inserted through the opening. A surgical staple or suture is used to abut and attach the flap to its original position in the anulus.

The above described implantation method is preferably performed via a posterior approach. Additionally, the flap created in the anulus does not destroy or otherwise prevent the anulus from healing. In fact, the flap promotes the healing of the anulus. Further, by placing the flap along the same plane or orientation as the plies which make up the anulus, the constraining ability of the anulus is at all times maintained.

BRIEF DESCRIPTION OF THE DRAWINGS

FIG. 5 is a transverse sectional view of an intervertebral discal area having the inflatable jack of FIG. 3 along with a properly positioned prosthetic holding and implanting tool in accordance with the method of the present invention.

FIG. 6 is a transverse sectional view of an intervertebral disc area having two prosthetic spinal disc nucleus bodies implanted in accordance with the method of the present invention.

FIG. 7 is a perspective view of the preferred spinal anulus cutter.

FIG. 8 is an exploded perspective view of the head of the preferred spinal anulus cutter.

FIG. 9 is an enlarged end view of the preferred spinal anulus cutter, with a mounting plug removed.

FIG. 10 is an enlarged sectional view of the preferred spinal anulus cutter of FIG. 9.

FIGS. 14–16 illustrate steps of fabricating the preferred prosthetic spinal disc nucleus body of FIG. 11.

DETAILED DESCRIPTION OF THE PREFERRED EMBODIMENTS

Figure 1:
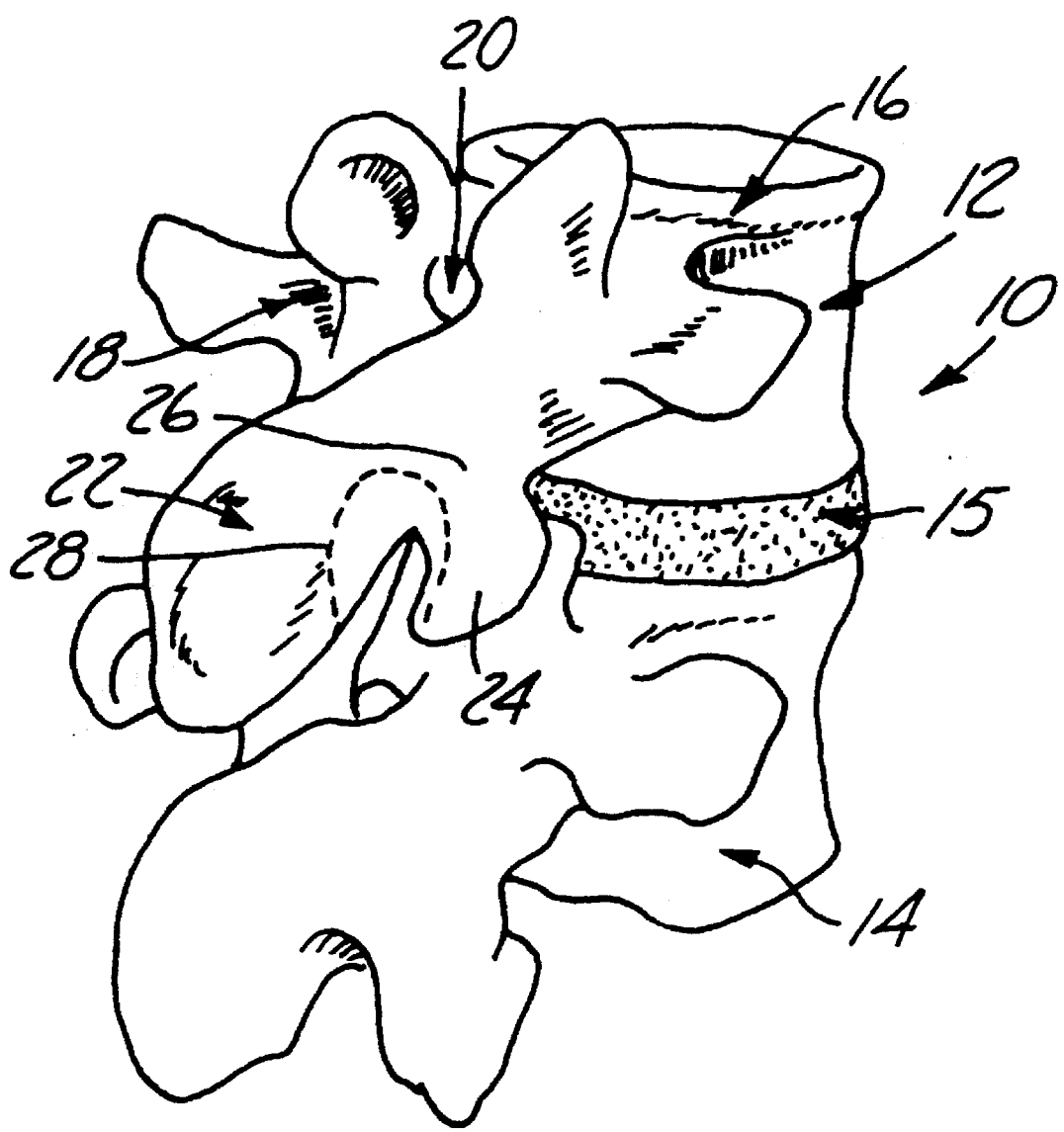
FIG. 1 is a perspective view of adjacent vertebrae showing the location of a minor laminectomy on one lamina in accordance with the preferred method of the present invention.

A preferred method of implanting a prosthetic spinal disc nucleus body is performed on a discal area 10, as shown in FIG. 1. The discal area 10 separates an upper vertebra 12 from a lower vertebra 14 and includes an anulus 15 and nucleus (not shown). The upper vertebra 12 has a vertebral body 16 from which a lamina bone 18 extends in a posterior direction. The lamina 18 surrounds the vertebral foramen 20 through which the spinal cord (not shown) passes. Extending generally in a posterior direction, the lamina 18 has a spinous process 22 and a inferior articular process 24 which extend downward, creating an arch-like structure 26 at the approximate level of the anulus 15. While FIG. 1 only depicts one arch-like structure 26 located to the right of the spinous process 22, the configuration of the lamina 18 is such that a similar arch-like structure (not shown) exists to the left of the spinous process 22. Notably, the arch-like structures 26 are located at a position posterior of the discal area 10 and on either side of the true sagittal plane of the discal area 10.

While the naturally occurring, arch-like structures 26 provide some access to the anulus 15, the preferred embodiment requires that a minor laminectomy be performed to broaden the arch-like structures 26 at specific targeted areas. As shown with a broken line at 28, a portion of the bony lamina 18 is removed so that various surgical instruments can pass through the arch-like structures 26 portion of the fully access the anulus 15 and discal area 10. The lamina 18 shown in FIG. 1 depicts only one laminectomy bore 28, located to the right of the spinous process 22. However, a similar bore (not shown) is likewise created to the left of the spinous process 22. Notably, the minor laminectomy need not be done where the arch-like structures 26 provide sufficient access to the anulus 15 in their natural form.

Figure 2:
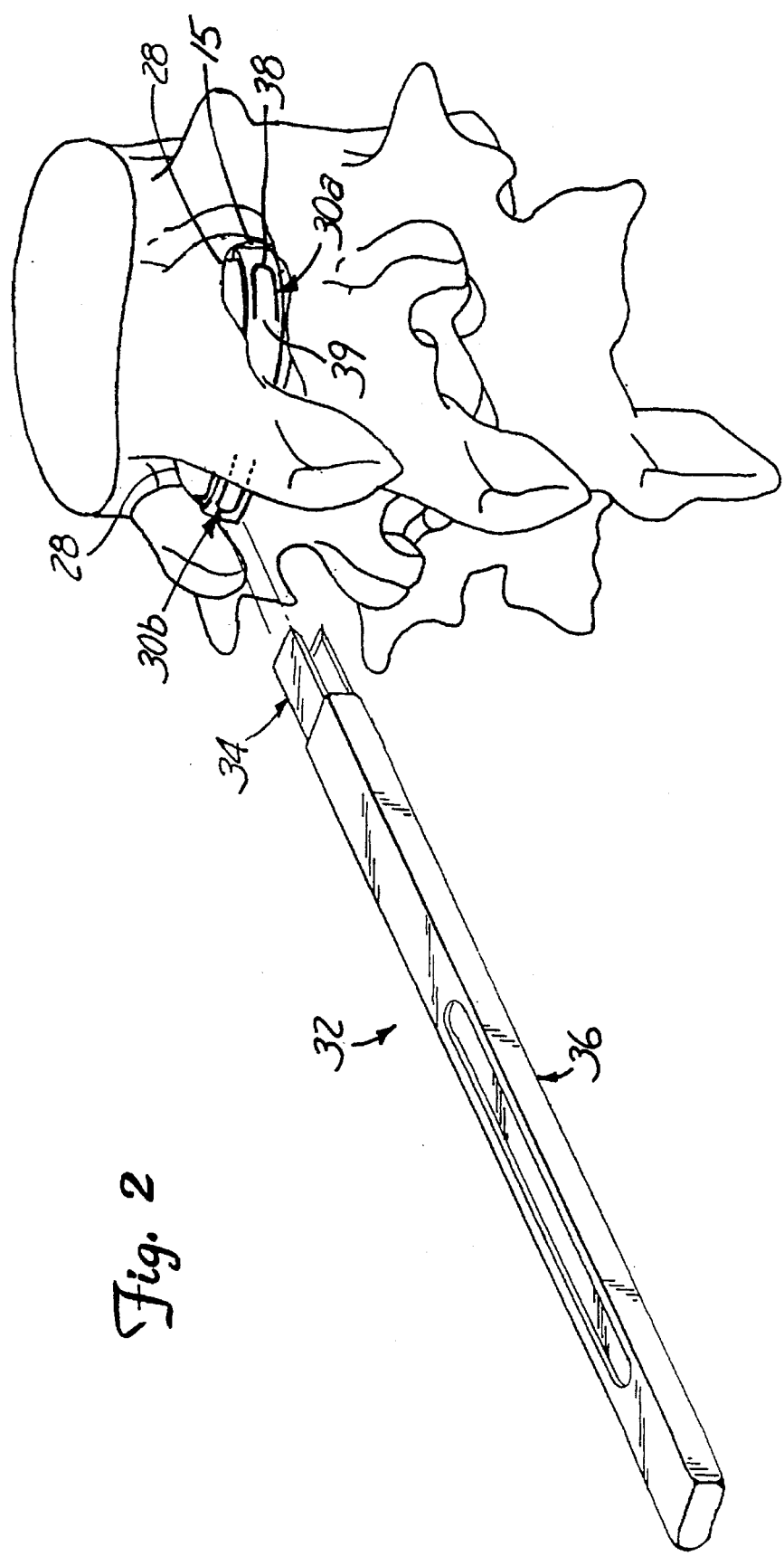
FIG. 2 is a perspective view of adjacent vertebrae showing a disc having C-shaped flaps created by a spinal anulus cutter in accordance with the method of the present invention.

Following the laminectomy procedure, the surgeon cuts a first flap 30*a* and a second flap 30*b* through the anulus 15 as shown in FIG. 2. The first flaps 30*a* and the second flap 30*b* are made by an spinal anulus cutter 32. The spinal anulus cutter 32 has a knife blade 34 and a handle 36. In a preferred embodiment, the knife blade 34 is curved or C-shaped. To create the first flap 30*a* and the second flap 30*b*, the knife blade 34 passes through the arch-like bores 28 created in the lamina 18 and contacts the posterior surface of the anulus 15. A hammer or similar device is used to drive the knife blade 34 through the anulus 15. Corresponding with the preferred C-shape of the knife blade 34, the first flap 30 a and the second flap 30*b* in the anulus 15 are C-shaped. Notably, when the spinal anulus cutter 32 is directed through the left or right bore 28 in the lamina 18, any portion of the spinal rootlets (not shown) contained within the vertebral foramen (not shown) which might otherwise impede the spinal anulus cutter 32 from contacting the anulus 15 are carefully moved aside.

The first flap 30a and the second flap 30b are positioned on the anulus 15 in symmetrical opposition to one another, and are approximately equidistance from the sagittal center of the disc space 10. Additionally, the first flap 30a and the second flap 30b are created to preferably extend away from the sagittal center of the anulus 15. For example, the first flap 30 a has a closed or curved portion 38 which is positioned distal to the sagittal center of the anulus 15 and an open portion 39 which is proximal to the sagittal center. The second flap 30b is similarly orientated. In this position, the anulus 15 tissue comprising the first flap 30a and the second flap 30b will open towards the sagittal center.

An additional feature of the flaps 30a and 30b is that their placement will not damage the tightness or constrainability of the anulus 15. The height of the first flap 30a and the second flap 30b, defined by the lateral edges of the closed or curved portion 38, is less than the transverse height of the anulus 15. Thus, as the entire transverse height of the anulus 15 is not severed, the upper and lower portions of the anulus 15 maintain their tightness around the nucleus. Further, only a small portion of the anulus tissue 15 is upset as the flaps are configured to follow the predisposed orientation of the anulus plies.

In the preferred embodiment the first flap 30a and the second flap 30b have a height of 0.25 inches and a length of 0.75 inches. The curved portion 38 has a radius of curvature of 0.125 inches. Successful implantation can also be achieved using flaps 30a and 30b of varying dimensions, such as an increased length. Additionally, the first flap 30a and the second flap 30b need not be curved, but instead can assume any other shape, so long as a closed side 38 and an open side 39 is provided. For example, the closed end 38 may be a straight, angled, serrated, etc. Further, the knife blade 34 can create a plurality of flaps, as when it is H-shaped or Y-shaped.

Figure 3:
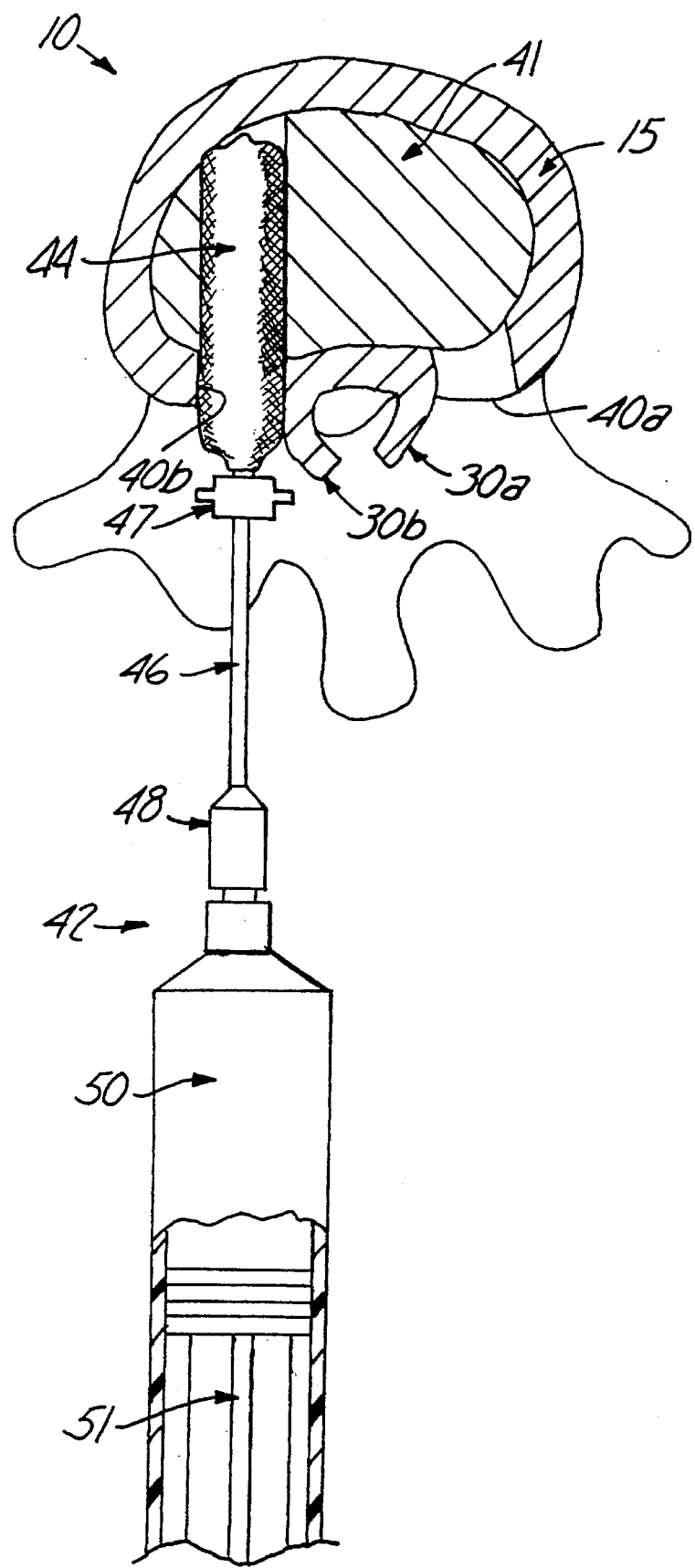
FIG. 3 is a transverse sectional view of an intervertebral discal area having a properly positioned inflatable jack in accordance with the method of the present invention.

The newly formed flaps 30a and 30b are opened to provide access to the nucleus 41. This is accomplished by grasping the closed end 38 and simply folding or peeling the first flap 30a and the second flap 30b back in a posterior direction toward the sagittal center of the discal area 10. The open end 39 acts as a pivot point for the flap 30a or 30b as it is folded back. Once fully retracted, the first flap 30a and the second flap 30b are held open via a surgical device such as a clamp to create a first opening 40a and a second opening 40b, respectively, as shown in FIG. 3. The nucleus 41 is accessed through the first opening 40a and/or the second opening 40b and enough material is removed to provide sufficient space in the material within the anulus 15 for prosthetic implantation. This removal can take place by way of a standard surgical suction device or other surgical methods, such as a pituitary rongeur or a curette, capable of removing the material within the anulus 15.

The vertebrae above and below the damaged discal area 10 are forced apart slightly by way of an inflatable jack 42. The inflatable jack 42 has a membrane or balloon 44 which is sealed around a distal end of a flexible fluid supply tube 46. The fluid supply tube 46 has a control valve 47, preferably a luer-lock two way valve, which provides independent control of fluid entering and exiting the balloon 44. Additionally, the fluid supply tube 46 has on its proximal end a valve 48 which allows fluid to enter the balloon 44 and can also act to prevent its release. Finally, the valve 48 is attached to a fluid actuator 50, including flexible tubing 51, which forces fluids, such as air, through the fluid supply tube 46 into the balloon 44, causing it to expand.

In the preferred embodiment, the balloon 44 is made from an arterial prosthesis and is coated with silicone. The rigid fluid supply tube 46 is 0.125 inch diameter stainless steel tubing and is approximately 2 inches in length. The valve 48 is also made from a surgically safe material. Finally, the fluid actuator 50 is a standard injection regulator as normally employed for angioplasty inflation, and includes 1 foot of flexible tubing 51. The above-described configuration of the inflatable jack 42 may be altered both dimensionally and in actual make-up.

Prior to insertion into the surrounded by the anulus 15, the balloon 44 is deflated. The deflated balloon 44 is of a dimension small enough to fit through the first opening 40a or the second opening 40b in the anulus 15 and is directed into the area once occupied by the nucleus 41 through the opening (40b in FIG. 3). The control valve 47 lies outside of the anulus 15 so that the surgeon can easily control the fluid level within the balloon 44. The balloon 44 is then inflated, causing the vertebrae adjacent to the discal area 10 to slightly separate, or jack apart. Normally, a pressure of 8 ATM is sufficient to achieve the required vertebrae separation. The inflatable jack 42 and adjacent vertebrae are then "locked" in this position by closing the control valve 47 and the valve 48.

With the vertebrae adjacent to the discal area 10 sufficiently separated, a prosthetic spinal disc nucleus body is inserted through the opening (40a in FIG. 3) not otherwise occupied by the inflatable jack 42. Notably, while FIG. 3 depicts the inflatable jack 42 passing through the second opening 40b, this positioning can be reversed.

Figure 4:
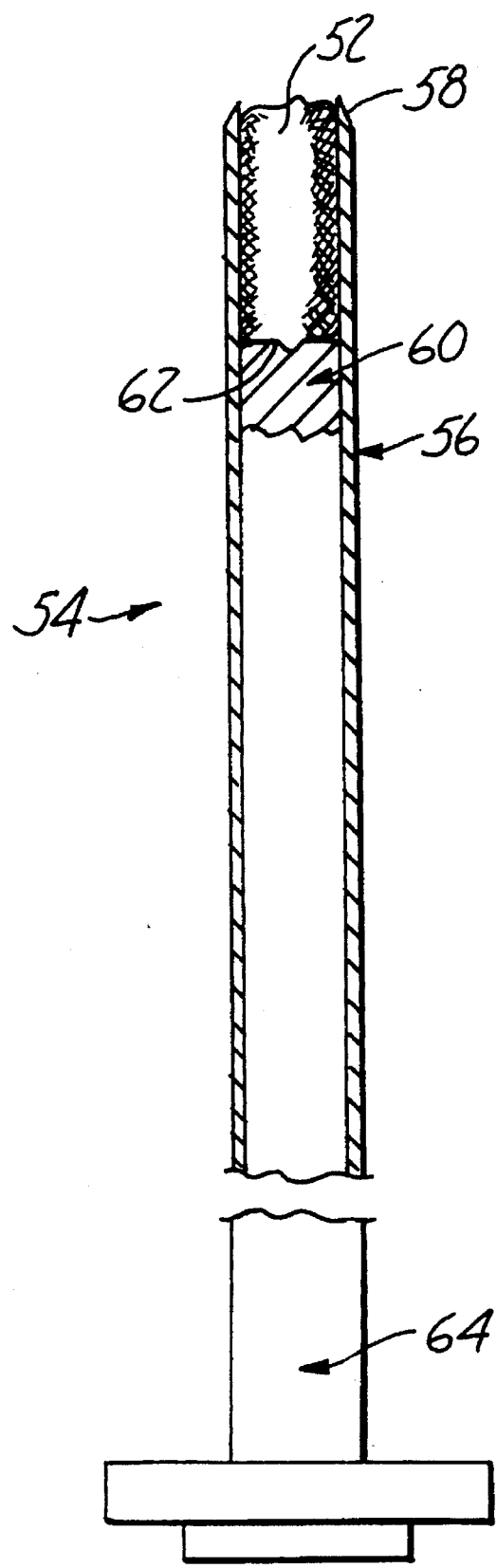
FIG. 4 is a cross sectional view of a prosthetic holding and implanting tool in accordance with the method of the present invention.

Prior to implant, the prosthetic spinal disc nucleus body 52 is stored axially within a prosthetic holding tube 54. As shown in FIG. 4, the prosthetic holding tube 54 has an outer cylinder 56 which is tapered on its exit end 58. Within the outer cylinder 56 is the prosthetic spinal disc nucleus body 52a and an ejection plunger 60. The ejection plunger 60 has an end 62 which is designed to correspondingly abut with the prosthetic spinal disc nucleus body 52. Finally, the ejection plunger 60 has an outer handle 64 which extends away from the cylinder 56. Prior to implant, the ejection plunger 60 is retracted such that the prosthetic spinal disc nucleus body 52 is fully enclosed within the outer cylinder 56. The prosthetic spinal disc nucleus body 52 is extricated from the holding tube 54 by simply moving the ejecting plunger 60 forward until the prosthetic body 52 is clear of the outer cylinder 56.

As shown in FIG. 5, a first prosthetic spinal disc nucleus body 52a is implanted into the area once occupied by the nucleus 41 by directing the prosthetic holding tube 54 through the opening (40a in FIG. 5) in the anulus 15 not otherwise occupied by the inflatable jack 42. Preferably, while the height of the first prosthetic nucleus body 52a is greater than the height of the first opening 40a or the second opening 40b the holding tube 54 will easily pass through the first opening 40a or the second opening 40b due to the tapered configuration of the exit end 58 of the holding tube 54. Once the exit end 58 of the prosthetic holding tube 54 is properly positioned, a force is placed on the outer handle 64 to press forward the ejection plunger 60 and axially eject the first prosthetic nucleus body 52a into the nucleus 41. The ejection plunger 60 is then retracted and disengaged from the first prosthetic nucleus body 52a and the prosthetic holding tube 54 is removed from the opening (40a in FIG. 5).

Retropulsion of the first prosthetic spinal disc nucleus body 52a through the opening (40a in FIG. 5) is avoided as the height of the opening 40a or 40b is less than the height of the prosthetic spinal disc nucleus body 52a. With the first prosthetic nucleus body 52a in position, the inflatable jack 42 can then be removed. This is accomplished by deflating the balloon 44 until the vertebrae adjacent to the discal area 10 are supported by the previously inserted first prosthetic nucleus body 52a. Notably, this spacing will be at approximately 70 percent of the spacing provided by the jack. The inflatable jack 42 is then retracted through the anulus 15.

A second prosthetic spinal disc nucleus body (not shown) is inserted into the opening (40b in FIG. 5) in the anulus 15 previously occupied by the inflatable jack 42. This is accomplished in a fashion similar to that used for implanting the first prosthetic spinal disc nucleus body 52a through the use of a prosthetic holding tube 54 inserted into the remaining opening (40b in FIG. 5).

As shown in FIG. 6, the surgical clamp used to restrain the flaps 30a and 30b in the anulus 15 are removed once the first and second prosthetic nucleus bodies 52a and 52b are in place. Subsequently, the first flap 30a and the second flap 30b are replaced into full contact with the anulus 15 by a surgical suture, staple, or other means such as "tissue glue" (a human plasma cryoprecipitate and thumbian mixture, or equivalent), thus closing the first opening 40a and the second opening 40b.

Spinal Anulus Cutter Detail

FIGS. 7–10 depict in more detail the preferred spinal anulus cutter tool. A preferred embodiment of the spinal anulus cutter 110 is shown in FIG. 7. The spinal anulus cutter 110 is comprised of a handle 112 and a knife blade 114. The handle 112 has a grip 116, a shank 118 and a head 120. The grip 116 has a proximal end 122. The grip 116 is integrally attached to the shank 118 which in turn is integrally attached to the head 120. The knife blade 114 is mounted to the head 120 and extends forwardly. The knife blade 114 has a cutting edge 124 on its forward end.

The grip 116 is preferably made of a plastic material, such as polycarbonate, and is formed by standard plastic molding techniques. Other rigid, lightweight materials are equally suitable. The grip 116, which is shown in FIG. 7 as being a substantially rectangular cylinder, preferably has an axial length of about 200 millimeters (8 inches), a width of about 14 millimeters (0.55 inches) and thickness of about 8 millimeters (0.3 inches). For identification purposes, the grip 116 is provided with a rounded side 126, which corresponds with a rounded side of the knife blade 114. While details of the knife blade 114 are provided below, it is sufficient to note that the curved side 126 allows a user of the spinal anulus cutter 110 to identify the orientation of the knife blade 114 by "feeling" the rounded side 126 of the grip 116. Any other shape, such as circular, square, etc. or size which promotes the simple grasping and handling of the spinal anulus cutter 110 can be used.

The proximal end 122 of the grip 116 is preferably relatively flat in a plane perpendicular to the axial length of the handle 112, but can also be rounded. Additionally, a uniform indentation 128 is provided along either side of the grip 116. The indentation 128 is preferably obround in configuration and has a length of approximately 125 millimeters (5 inches). The indentation 128 is provided to assist in grasping the handle 112 and to provide an area for various manufacturer nomenclature.

The shank 118 is integrally attached to the grip 116 and extends in an axial fashion therefrom. In the preferred embodiment, the shank 118 and the grip 116 are manufactured as a single piece. However, the shank 118 and the grip 116 can be produced as separate bodies, later mounted to one another via various mounting techniques. The shank 118 has an axial length of about 75 millimeters (3 inches) and a width and thickness similar to that of the grip 116. Further, the shank 118 has a rounded side (not shown) corresponding with the rounded side 126 of the grip 116. Alternatively, other geometrical configurations, such as circular or square, can be used. Similarly, any other length, either longer or shorter, is acceptable so long as sufficient clearance between the knife blade 114 and the proximal end 122 of the grip 116 is provided.

The shank 118 is preferably made of a plastic material, such as polycarbonate, similar to that of the grip 116. Alternatively, other surgically safe materials, such as aluminum, may be employed which maintain the rigidness of the shank 118 during use.

The shank 118 is integrally attached to the head 120. In the preferred embodiment, the head 120 and shank 118 are formed as a single piece. However, the head 120 and the shank 118 may be produced separately and later mounted via various mounting techniques.

The head 120 is preferably made of a plastic material, such as polycarbonate, and extends axially from the shank 118. As shown in FIG. 8, the head 120 conforms in shape to the shank 118, being generally rectangular with a rounded side 126. The head 120 has an opening 130 for receiving the knife blade 114. The opening 130 is of a configuration generally conforming to the outer surface of the head 120. In other words, the opening 130 is of a generally rectangular shape with one side being arcuate. The opening 130 is approximately 15 millimeters (0.5 inches) deep. A bore 132 extends rearwardly from the opening 130 in the head 120. The bore 132 is cylindrical in shape, having a diameter of about 3 millimeters (0.125 inches) and a length of about 15 millimeters (0.5 inches).

The knife blade 114 nests within the opening 130 of the head 120 and is comprised of a plurality of walls connected to one another. In a preferred embodiment, a continuous wall 134 is formed, extending forwardly from the head 120. The cutting edge 124 is formed at the forward edge of the wall 134 and has a cutting angle of approximately 22° or less. The continuous wall 134 is formed to approximate an arch shape having a closed side 136, a first extending side 138a and second extending side 138b, and an open side 140. In the preferred embodiment, the closed side 136 is curved to generally form a C-shape.

More specifically, in the preferred embodiment, the closed side 136 of the continuous wall 134 is defined by a 180 degree arc from which the first extending side 138a and the second extending side 138b project parallel to one another. The side 140 opposite the closed side 136 is open. With this configuration, the knife blade 114 creates an aperture 142 defined by the internal side of the continuous wall 134. The flap formed by the knife blade 114 will conform in shape and size with the aperture 142.

The distance between the first extending side 138a and the second extending side 138b is approximately 6 millimeters (0.25 inches). The radius of curvature of the closed, curved side 136 is approximately 3 millimeters (0.125 inches). As shown in FIG. 8, the blade wall 134 nests within the head 120. When the knife blade 114 is properly positioned, the length of the aperture 142, running from a leading edge 144 of the head 120 to the cutting edge 124 of the knife blade 114, is approximately 20 millimeters (0.75 inches). Finally, the width of both the first extending side 138a and the second extending side 138b is approximately 13 millimeters (0.5 inches).

While the knife blade 114 has been described as preferably having a generally curved or C-shape, other similar configurations are acceptable. For example, the closed side 136 need not be curved and instead may be flat, angled or serrated. In addition, other dimensions for the knife blade 114 may be employed so long as at least one multisided flap of a size sufficient to provide access to the nucleus is substantially simultaneously cut by the cutting edge 124. Basically, this requires that the knife blade 114 have at least two sides 138a and 138b which are connected on one side 136 and open on the other 140. As the knife blade 114 passes through the encapsulating ligament, such as this anulus, the open side 140 will not cut the ligament material and thus forms the "pivot point" for the flap. The cutting edge 124 is therefore a pair of spaced end points connected by a continuous, nonlinear path or wall. Alternatively, a plurality of flaps may be formed, such as by an "H"-shaped or "Y"-shaped knife blade.

The knife blade 114 is preferably made of 420 stainless steel. Alternatively, any other type of surgically safe metal can be used, such as 17-4 stainless steel, titanium, surgical steel, etc.

The knife blade 114 is mounted within the opening 130 of the head 120 by way of a plug 146. The plug 146 is comprised of a distal member 148 and a proximal member 150. The proximal member 150 is of a size and configuration similar to the bore 132 of the head 120. The distal member 148 is of a size and configuration similar to the opening 130.

As shown in FIGS. 9 and 10, the knife blade 114 has a proximal end 152 from which a first tab 154a and a second tab 154b extend inwardly. The first tab 154a and the second tab 154b project approximately 0.03 inches from the knife walls. Notably, the plug 146 is not depicted in FIG. 9 to better illustrate the shape of the first tab 154a and the second tab 154b.

After the knife blade 114 is placed within the opening 130 of the head 120, the plug 146 is then inserted into the head 120 such that the proximal member 150 of the plug 146 nests within the bore 132 of the head 120. The distal member 148 of the plug 146 comes in contact with the first tab 154a and the second tab 154b, thus holding the knife blade 114 in place. In addition to a frictional fit, a solvent is used to maintain the plug 146 and knife blade 114 in this final position.

Prosthetic Spinal Disc Nucleus Detail

FIGS. 11-16 depict in more detail the preferred prosthetic spinal disc nucleus body.

Figure 11:
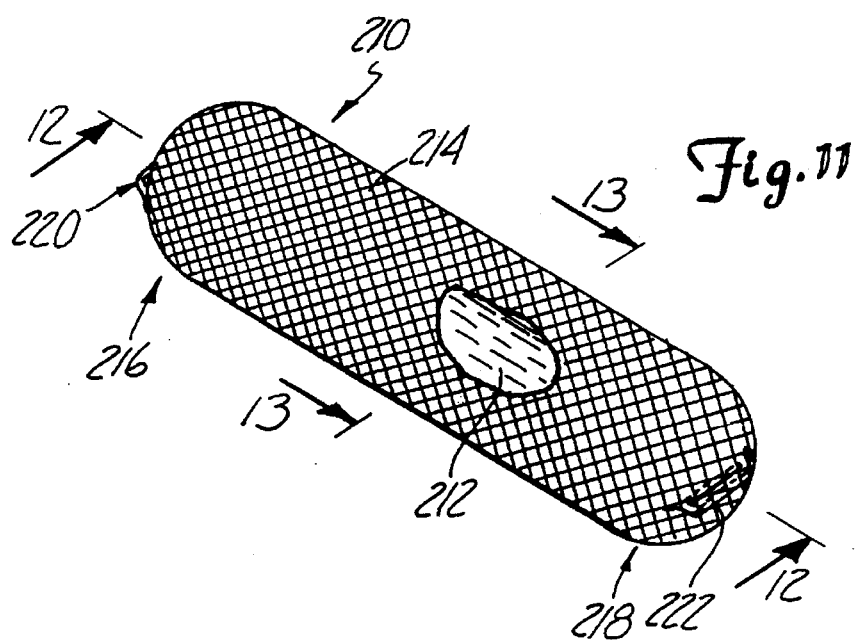
FIG. 11 is a perspective view of a preferred prosthetic spinal disc nucleus body, including a cutaway view showing a portion of a hydrogel material core.

A preferred embodiment of the prosthetic spinal disc nucleus body 210 is shown in FIG. 11. The prosthetic spinal disc nucleus body 210 is comprised of a hydrogel core 212 and a constraining jacket 214. The prosthetic spinal disc nucleus body 210 has an anterior end 216 and a posterior end 218. The constraining jacket 214 is secured around the hydrogel core 212 by an anterior closure 220 located at the anterior end 216 and a posterior closure 222 located at the posterior end 218.

Figure 12:
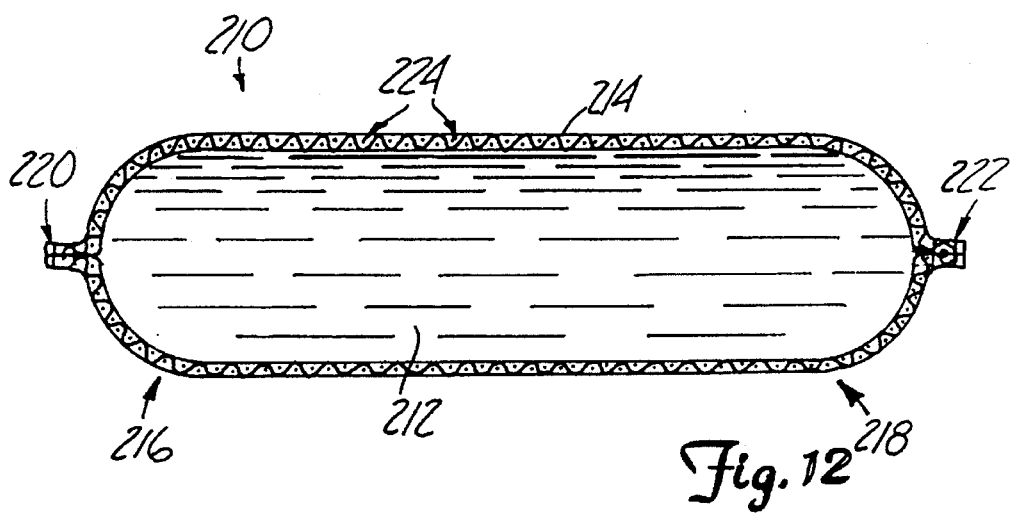
FIG. 12 is a side sectional view of the preferred prosthetic spinal disc nucleus body along the line 12—12 of FIG. 11.
Figure 13:
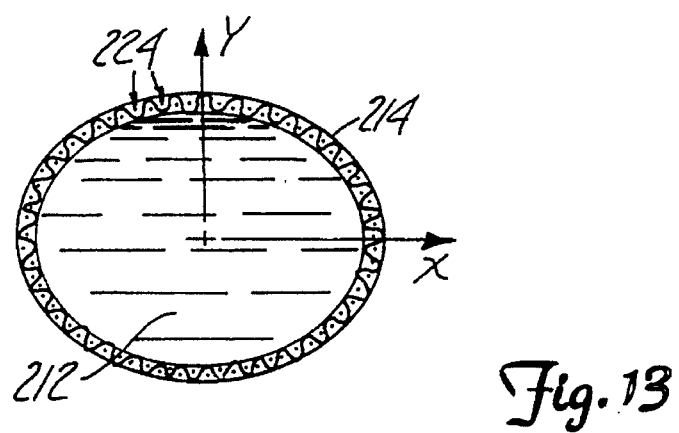
FIG. 13 is a frontal sectional view of the preferred prosthetic spinal disc nucleus body along the line 13—13 of FIG. 11.

As shown in FIGS. 12 and 13, the hydrogel core 212 is fabricated to assume a pillow shape. Along the longitudinal (or sagittal) plane (as shown in FIG. 12), the hydrogel core 212 has an obround configuration whereas the frontal plane (as shown in FIG. 13) is oval.

The preferred hydrogel core 212 is formulated as a mixture of hydrogel polyacrylonitrile. Alternatively, the hydrogel core 212 can be any hydrophilic acrylate derivative with a unique multiblock copolymer structure or any other hydrogel material having the ability to imbibe and expel fluids while maintaining its structure under various stresses. For example, the hydrogel core 212 can be formulated as a mixture of polyvinyl alcohol and water. Much like a normal human nucleus, the hydrogel core 212 will swell as it absorbs fluids. The hydrogel core 212 has a time constant of swelling which is highly similar to that of the natural nucleus and will thus experience a 5-30% and preferably a 15-20% volume change depending on load over the course of 2-8 (preferably 4-8) hours. When fully hydrated, the hydrogel core 212 will have a water content of between 25-65%. The hydrogel material 212 of the preferred embodiment is manufactured under the trade name Hypan® by Hymedix International, Inc.

Completely surrounding the hydrogel core 212 is the constraining jacket 214. The constraining jacket 214 is preferably a closed tube made of a tightly woven high molecular weight, high tenacity polymeric fabric. Further, the constraining jacket 214 is flexible. In a preferred embodiment, high molecular weight polyethylene is used as the weave material for the constraining jacket 214. However, polyester or any other high molecular weight, high tenacity material can be employed. For example, carbon fiber yarns, ceramic fibers, metallic fibers, etc. are acceptable.

The preferred woven construction of the constraining jacket 214 creates a plurality of small openings 224. These openings are large enough to allow bodily fluids to interact with the hydrogel core 212, which is maintained within the constraining jacket 214. However, the openings 224 are small enough to prevent the hydrogel 212 from escaping. Preferably, the openings 224 have an average diameter of about 10 micrometers, although other dimensions are acceptable. While the constraining jacket 214 is described as having a weave configuration, any other configuration having a semipermeable or porous attribute can be used.

By employing a flexible material for the constraining jacket 214, the hydrogel core 212 is allowed to expand and contract in a controlled fashion as it imbibes and expels fluids. When the hydrogel core 212 swells as a result of an influx of water, the constraining jacket 214 has sufficient flexibility to allow the hydrogel core 212 to expand. The strength and flexibility characteristics of the material used for the constraining jacket 214 are such that the pillow shape of the hydrogel 212 will always be maintained. By imparting a uniform constraining force on the surface of the hydrogel core 212, the constraining jacket 214 prevents undesired deformation of the prosthetic spinal disc nucleus body 210. However, for the prosthetic spinal disc nucleus body 210 to function as would a natural nucleus, some desired changes in the shape and size of the hydrogel core 212 must take place as loads are increased and decreased.

As fluids are imbibed, the woven constraining jacket 214 works in conjunction with the oval cross sectional shape of the hydrogel core 212 to control expansion of the hydrogel core 212. The prosthetic spinal disc nucleus body 210 initially assumes an oval shape in its frontal plane (as shown in FIG. 13). The nucleus body 210 will maintain this shape and act as a cushion against various loads placed upon it. As these loads are decreased (e.g. when the patient reclines), the hydrogel core 212 imbibes surrounding fluids and expands. The constraining jacket 214 ensures that this expansion is only in the form of the hydrogel core 212 becoming more circular in frontal cross section. In other words, the constraining jacket 214 allows the hydrogel core 212 to expand in the y-direction (vertically), but prevents a simultaneous expansion in the x-direction (horizontally). Further, while limited horizontal contraction will preferably occur, the vertical expansion proceeds at a proportionately greater rate than the horizontal contraction. Therefore, the smaller the load placed upon the prosthetic spinal disc nucleus body 210, the closer the body 210 is to a circular frontal cross section. To help achieve this unique effect, the preferred constraining jacket 214 is substantially inelastic. To prevent the hydrogel core 212 from escaping, the constraining jacket 214 has a burst strength which is greater than the swelling pressure of the hydrogel core 212 when fully hydrated.

FIGS. 14–16 illustrate the manufacturing of the prosthetic spinal disc nucleus body 210. First, the hydrogel core 212 is formulated. An appropriately sized volume of hydrogel material is dehydrated, resulting in an undersized, substantially cylindrical gel capsule. This dehydrated hydrogel material 212 is then inserted into the constraining jacket 214.

As shown in FIG. 14, the constraining jacket 214 is preferably tubular in shape with openings at both the anterior end 216 and the posterior end 218. The dehydrated hydrogel material 212 is placed within the constraining jacket 214 and centered between the anterior end 216 and the posterior end 218. The ends of the constraining jacket 214 are then secured by forming the anterior closure (not shown) and the posterior closure 222.

In the centered position, the hydrogel material core 212 will have a length smaller than that the of the constraining jacket 214 resulting in excess outer layer material 226 at both the anterior end 216 and the posterior end 218. The excess outer layer material 226 at both the anterior end 216 and the posterior end 218 is closed to prevent the hydrogel material 212 from escaping or leaking from the confines of the constraining jacket 214. As shown in FIGS. 15 and 16, to form the posterior closure 222, the excess outer layer material 226 is preferably folded or tucked and then closed. The fold is created by pinching two opposing sides of the excess material 226 centrally towards one another, approximating a "FIG. 8" form. The two remaining free ends are flattened against one another, resulting in an "H-shaped" fold as shown in FIG. 15.

The fold is then closed by sewing a dense, bar-tack stitch 228 across the folded section at a position near the hydrogel core 212. The bar-tack stitch 228 material is preferably the same high tenacity polymeric material, such as high molecular weight polyethylene, as is used for the constraining jacket 214. By employing the same material for both the constraining jacket 214 and the bar-tack stitch 228, the biocompatibility of the entire prosthetic spinal disc nucleus body 210 is ensured. The remaining excess material 226 is removed by a thermal cut made at a point distal to the bar-tack stitch 228. This thermal cut fuses the potentially fraying ends of the jacket, distal to the stitched portion 228.

While FIGS. 15 and 16 only show the posterior closure 222 on the posterior end 218, the excess material 226 on the anterior end 218 is folded and sealed in a similar fashion to form the anterior closure 220. Notably, it is not always necessary to fold the excess outer layer material 226, where the anterior end 216 and the posterior end 218 are simply sealed by the dense, bar-tack stitch 228 without folding the material 226. Further while the constraining jacket 214 has been described as having two openings, it may instead by manufactured with a single opening, either on an end or side, through which the hydrogel core 212 is inserted.

To aid in ensuring proper placement of the prosthetic spinal disc nucleus body 210 within the intervertebral disc space and to review the stability of the prosthetic disc body 210 during patient follow-ups, a radiopaque wire 230 is placed inside the constraining jacket 214 at either the anterior end 216 or the posterior end 218, or both or longitudinally along the length of the constraining jacket 214. The radiopaque wire 230 is visible in x-ray applications and is preferably made of a platinum-iridium material, but can be any other material having a radiopaque and biologically inert characteristics. The wire 230 is placed within the excess material 226 at the anterior end 216 or the posterior end 218 and is secured by the bar-tack stitch 228. Alternatively, a radiopaque thread can be woven into the constraining jacket 214 or a radiopaque material can be added to the hydrogel core 212.

In its final form, the prosthetic spinal disc nucleus body 210 will have lengths of about 15 to 25 millimeters and an outer diameter of about 6–15 millimeters. The preferred disc body 210 is 25 millimeters in length and 10 millimeters in outer diameter. These dimensions conform with the approximate length of the sagittal diameter and approximate height of an adult human disc nucleus space, respectively. It is realized that not all human discs are of the same size. Therefore, the prosthetic spinal disc nucleus body 210 alternatively is constructed to assume dimensions of 20 millimeters in length and 10 millimeters in outer diameter; 25 millimeters in length and 7 millimeters in outer diameter; and 20 millimeters in length and 7 millimeters in outer diameter. Notably, other sizes are possible. The appropriate prosthetic disc for a particular patient is determined by various diagnostic procedures prior to and during surgery. Basically, the properly dimensioned prosthesis is a function of the patient's size and spinal level. By providing prosthetic spinal disc nucleus bodies 210 with varying dimensions, the space requirements reflected by any spinal segment, human or animal, are satisfied.

Following closure of the constraining jacket 214 about the hydrogel core 212, the prosthetic spinal disc nucleus body 210 is rehydrated and then subjected to compressive loads or "conditioned". The conditioning amounts to a series of at least three compressive loads being applied across the length of the prosthetic body 210. The magnitude of in vivo compressive loads will vary from patient to patient and is a function of the patient's size and spinal level. For example, published literature has stated that the normal sitting or standing compressive load on the discal area is 1.8 multiplied by the patient's body weight. Further, the maximum compressive load placed upon the lumbar discal area during usual, daily activities is 3.6 multiplied by the patient's body weight. The conditioning, therefore, will consist of a series of compressive loads being placed upon the prosthetic body 210 equivalent to a minimum of 1.8 multiplied by the typical body weight up to a maximum of 3.6 multiplied by the typical body weight. Following conditioning, the hydrogel core 212 will consistently return to its desired shape and size following the application and removal of compressive loads.

As a further benefit, the hydrogel 212 and its manufacturing process place volume expansion constraints on the hydrogel 212. Even if the hydrogel 212 were unconstrained (e.g. if the constraining jacket 214 ruptures), following conditioning the hydrogel 212 will not expand to more than about twice its volume. Thus, a continuous, unlimited, potentially hazardous swelling of the hydrogel 212 will not occur should the constraining jacket 214 be disrupted. This internalized constraint will also prevent possible over expansion of the hydrogel core 212 if the prosthetic spinal disc body 210 is continually unloaded in the disc space or if the prosthetic disc body 210 were to be displaced into another body cavity such as the spinal canal or abdomen.

The conditioning renders the prosthetic spinal disc nucleus body 210 to a partially flattened or oval shape. For example, a prosthetic body 210 originally having a diameter of about 10 millimeters will have a height of about 7 millimeters and width of about 14 millimeters following conditioning. Similarly, conditioning will alter a prosthetic body 210 having an original diameter of about 7 millimeters to one having a height of about 5 millimeters and a width of about 12 millimeters. The conditioned prosthetic spinal disc nucleus body 210 is then inserted into a retaining tube to maintain this oval shape up until implantation. The retaining tube is preferably made of implantable grade stainless steel, but can be any other surgically safe material such as polyethylene. The prosthesis 210 and its retaining tube may be packaged, surrounded by sterile water, saline or physiological solution (Ringer's). The entire surgical package is sterilized in a tray, via gamma, steam or other type of sterilization. Once conditioned, retained, and sterilized, the prosthetic spinal disc nucleus body 210 is ready for implantation into the human disc space.

The surgical method of the present invention does not destroy the anulus or its tightening ability around the discal area. The use of easily repairable flaps allows the anulus to heal quickly, providing the patient with an expedient recovery. Additionally, the surgical method of the present invention provides a viable, posterior approach, thus avoiding any damage to vital human organs often times arising during anterior implantation while supplying the surgeon clear access to the implant area. Finally, by using openings in the anulus which are smaller than the prosthetic spinal disc nucleus bodies, the chances of retropulsion of the bodies back through the anulus is greatly diminished.

Although the present invention has been described with reference to preferred embodiments, workers skilled in the art will recognize that changes may be made in form and detail without departing from the spirit and scope of the invention. For example, the flaps need not be curved, but can assume the form of any opening large enough to allow the prosthetic spinal disc nucleus body to be inserted into the disc area. Additionally, the prosthetic body is not required to be capsule or pillow shaped. The prosthetic body can be any shape or size and in fact may be of one size prior to implant, later expanding in size after implant. While the preferred embodiment described the implantation of two prosthetic bodies, it is possible to use any other number. For example, a single prosthetic body could be implanted through a single flap. Similarly, three or more prosthetic bodies could be inserted through an equal number of flaps. Finally, while the surgical method has been described as using a posterior approach, a lateral or anterior approach is equally applicable. Notably, when using the lateral or anterior approach, the previously described laminectomy is no longer necessary.

What is claimed is:

1. A surgical procedure for implanting a prosthetic spinal disc nucleus body into a human disc space, the procedure comprising:

exposing an anulus comprised of fibrous tissue positioned between adjacent vertebrae;

making an incision through the fibrous tissue of the anulus to form a flap comprised of the fibrous anulus tissue wherein a portion of the flap remains attached to the anulus;

maneuvering the flap to provide an opening;

inserting a prosthetic spinal disc nucleus body through the opening; and securing the flap to the anulus to close the opening.

2. The surgical procedure of claim 1 wherein the incision is made through a posterior side of the anulus.

3. The surgical procedure of claim 1 wherein the flap is C-shaped.

4. A surgical procedure for implantation of two prosthetic spinal disc nucleus bodies side-by-side into a human disc space, the procedure comprising:

exposing an anulus comprised of fibrous tissue positioned between adjacent vertebrae;

cutting the fibrous tissue of the anulus to form a first flap comprised of the fibrous anulus tissue, wherein a portion of the first flap remains attached to the anulus;

cutting the fibrous tissue of the anulus to form a second flap comprised of the fibrous anulus tissue wherein a portion Of the second flap remains attached to the anulus;

maneuvering the first flap to provide a first opening through the anulus;

inserting a first prosthetic spinal disc nucleus body into the human disc space through the first opening;

maneuvering the second flap to provide a second opening through the anulus; and inserting a second prosthetic spinal disc nucleus body into the human disc space through the second opening.

5. The surgical procedure of claim 4, wherein the first flap and the second flap are cut on a posterior side of the anulus, near a sagittal center of the disc.

6. The surgical procedure of claim 4 wherein the first flap and the second flap are symmetric with respect to a sagittal center of the disc.

7. The surgical procedure of claim 4 wherein the anulus has a transverse height and the first flap and the second flap each have a height less than the transverse height of the anulus.

8. The surgical procedure of claim 4 wherein the first flap and the second flap have a height of about 0.25 inches and a length of about 0.75 inches.

9. The surgical procedure of claim 8 wherein the first flap and the second flap are C-shaped and have a radius of curvature of about 0.125 inches.

10. The surgical procedure of claim 4 further including:

removing at least a portion of material located within the anulus prior to inserting the first prosthetic spinal disc nucleus body and the second prosthetic spinal disc nucleus body.

11. The surgical procedure of claim 4 further including:

12. The surgical procedure of claim 4 and further including:

inserting a jack into the disc space through the second opening in the anulus prior to inserting the first prosthetic spinal disc nucleus body;

separating the adjacent vertebrae by activating the jack; and removing the jack from the disc space prior to inserting the second prosthetic spinal disc nucleus body.

13. The surgical procedure of claim 4 wherein the disc space has a sagittal plane parallel to which the first and second prosthetic spinal disc nucleus bodies are inserted.

14. The surgical procedure of claim 4 further including securing the first flap and the second flap to the anulus after inserting the first prosthetic spinal disc nucleus body and the second prosthetic spinal disc nucleus body.

15. The surgical procedure of claim 4 wherein the first and second prosthetic spinal disc nucleus bodies have an obround configuration in two planes and an oval configuration in a third plane.

16. The surgical procedure of claim 4 and further including:

performing a minor laminectomy, before cutting the first flap or the second flap through the anulus, when a lamina bone partially surrounds a posterior portion of the disc space.

17. A surgical procedure for implantation of two prosthetic spinal disc nucleus bodies side-by-side into a human disc space defined by adjacent vertebrae, an anulus comprised of a fibrous tissue with a posterior side, and a nucleus, the procedure comprising:

exposing the posterior side of the anulus;

cutting the posterior side of the fibrous tissue of the anulus to form a first flap comprised of the fibrous anulus tissue, wherein a portion of the first flap remains attached to the anulus;

cutting the posterior side of the fibrous tissue of the anulus to form a second flap comprised of the fibrous anulus tissue, wherein a portion of the second flap remains attached to the anulus;

maneuvering the first flap to provide a first opening through the anulus;

maneuvering the second flap to provide a second opening through the anulus;

removing at least a portion of the nucleus through either the first opening or the second opening;

inserting a jack through the first opening in the anulus;

separating the adjacent vertebrae with the jack;

inserting a first prosthetic spinal disc nucleus body through the second opening in the anulus;

removing the jack;

inserting a second prosthetic spinal disc nucleus body through the first opening in the anulus;

securing the first flap to the anulus; and securing the second flap to the anulus.

* * * * *

UNITED STATES PATENT AND TRADEMARK OFFICE
CERTIFICATE OF CORRECTION

PATENT NO. : 5,562,736

DATED : OCTOBER 8, 1996

INVENTOR(S) : CHARLES D. RAY, EUGENE A. DICKHUDT

It is certified that error appears in the above-indentified patent and that said Letters Patent is hereby corrected as shown below:

Col. 2, line 57, delete "flay", insert --fray--

Col. 4, line 38, after "26" delete "portion of the", insert --and--

Col. 4, line 39, after "15" delete "and", insert --portion of the--

Col. 14, line 3, delete "Of", insert --of--

Col. 14, line 34, after "including:", insert -- separating the adjacent vertebrae prior to inserting the first prosthetic spinal disc nucleus body and the second prosthetic spinal disc nucleus body. --.

Signed and Sealed this

Twenty-fifth Day of March, 1997

Attest:

BRUCE LEHMAN

Attesting Officer

Commissioner of Patents and Trademarks